(12) United States Patent
Subkowski et al.

(10) Patent No.: US 8,710,096 B2
(45) Date of Patent: Apr. 29, 2014

(54) DETECTION AND USE OF LOW MOLECULAR-WEIGHT MODULATORS OF THE COLD-MENTHOL RECEPTOR TRPM8

(75) Inventors: Thomas Subkowski, Ladenburg (DE); Claus Bollschweiler, Heidelberg (DE); Jens Wittenberg, Limburgerhof (DE); Michael Krohn, Lorsch (DE); Holger Zinke, Zwingenberg (DE)

(73) Assignee: BASF SE, Ludwigshafen (DE)

( * ) Notice: Subject to any disclaimer, the term of this patent is extended or adjusted under 35 U.S.C. 154(b) by 395 days.

(21) Appl. No.: 13/060,323

(22) PCT Filed: Aug. 26, 2009

(86) PCT No.: PCT/EP2009/061019
§ 371 (c)(1),
(2), (4) Date: Feb. 23, 2011

(87) PCT Pub. No.: WO2010/026094
PCT Pub. Date: Mar. 11, 2010

(65) Prior Publication Data
US 2011/0145970 A1 Jun. 23, 2011

(30) Foreign Application Priority Data
Aug. 26, 2008 (EP) .................... 08162997

(51) Int. Cl.
*A61K 31/00* (2006.01)
*A61Q 11/00* (2006.01)

(52) U.S. Cl.
CPC .......... *A61K 31/00* (2013.01); *A61K 2800/244* (2013.01); *A61Q 11/00* (2013.01); *A61K 2800/78* (2013.01)
USPC .......................................... 514/449; 514/176

(58) Field of Classification Search
USPC ....................... 514/415, 449, 463; 424/78.38
See application file for complete search history.

(56) References Cited

U.S. PATENT DOCUMENTS

| | | | |
|---|---|---|---|
| 2003/0207904 A1 | 11/2003 | Wei | |
| 2004/0028714 A1 | 2/2004 | Blondeau et al. | |
| 2005/0084447 A1 | 4/2005 | Wei | |
| 2006/0167263 A1 | 7/2006 | Wilde et al. | |

FOREIGN PATENT DOCUMENTS

| CH | 651445 A5 | 9/1985 |
|---|---|---|
| EP | 1913976 A1 | 4/2008 |
| EP | 1958627 A2 | 8/2008 |
| EP | 2033688 A2 | 3/2009 |
| RU | 704083 C | 10/1993 |
| SU | 636236 A1 | 12/1978 |
| SU | 776048 A1 | 9/1983 |
| SU | 704082 A1 | 10/1989 |
| WO | WO-9956548 A1 | 11/1999 |
| WO | WO-0200590 A1 | 1/2002 |
| WO | WO-02/15692 A1 | 2/2002 |
| WO | WO-04/000023 A1 | 12/2003 |
| WO | WO-2004/026840 A1 | 4/2004 |
| WO | WO-2005/099711 A1 | 10/2005 |
| WO | WO-2006040136 A1 | 4/2006 |
| WO | WO-2007/017093 A1 | 2/2007 |
| WO | WO-2007/019719 A1 | 2/2007 |
| WO | WO-2007048265 A1 | 5/2007 |
| WO | WO-2008/015403 A1 | 2/2008 |
| WO | WO-2009/064388 A2 | 5/2009 |
| WO | WO-2010010435 A2 | 1/2010 |
| WO | WO-2010026094 A1 | 3/2010 |

OTHER PUBLICATIONS

Andersson et al., Jour. Neurosci, 2004, 24(23, 5364-5369.*
DD McKemy, 2007, Chapter 13, TRPM8: The Cold and Menthol Receptor. In: Liedtke WB, Heller S, editors. TRP Ion Channel Function in Sensory Transduction and Cellular Signaling Cascades. Boca Raton (FL): CRC Press.*
Beck, B., et al., "Prospects for Prostate Cancer Imaging and Therapy Using High-Affinity TRPM8 Activators", Cell Calcium, vol. 41, (2007), pp. 285-294.
Behrendt, H.-J., et al., "Characterization of the Mouse Cold-Menthol Receptor TRPM8 and Vanilloid Receptor Type-1 VR1 Using a Fluorometric Imaging Plate Reader (FLIPR) Assay", British Journal of Pharmacology, vol. 141, (2004), pp. 737-745.
Dhaka, A., et al., "TRP Ion Channels and Temperature Sensation", Annu. Rev. Neurosci., vol. 29, (2006), pp. 135-161.
Furrer, S. M., et al., "New Developments in the Chemistry of Cooling Compounds", Chem. Percept., vol. 1, (2008), pp. 119-126.
Lashinger, E.S.R., et al., "AMTB, a TRPM8 Channel Blocker: Evidence in Rats for Activity in Overactive Bladder and Painful Bladder Syndrome", Am. J. Physiol Renal Physiol, vol. 295, (2008), pp. F803-F810.
Levine, J. D., et al., "TRP Channels: Targets for the Relief of Pain", Biochimica et Biophysica Acta, vol. 1772, (2007), pp. 989-1003.
McKemy, D.D., "How Cold Is It? TRPM8 and TRPAI in the Molecular Logic of Cold Sensation", Molecular Pain, vol. 1, No. 16, (2005), pp. 1-7.
McKemy, D. D., et al., "Identification of a Cold Receptor Reveals a General Role for TRP CHannels in Thermosensation", Nature, vol. 416, (2002), pp. 52-58.
Mukerji, G., et al., "Pain During Ice Water Test Distinguishes Clinical Bladder Hypersensitivity From Overactivity Disorders", BMC Urology, vol. 6, No. 31, (2006), pp. 1-7.
Peier, A., et al., "A TRP Channel That Senses Cold Stimuli and Menthol", Cell, vol. 108, (2002), pp. 705-715.

(Continued)

*Primary Examiner* — Ernst Arnold
*Assistant Examiner* — Kauser M Akhoon
(74) *Attorney, Agent, or Firm* — Novak Druce Connolly Bove + Quigg LLP

(57) ABSTRACT

The invention relates to novel modulators of the cold menthol receptor TRPM8, to a method for modulating the TRPM8 receptor using said modulators; to the use of the modulators for induction of cold sensation; and to objects and means produced using said modulators.

20 Claims, 4 Drawing Sheets

(56) References Cited

OTHER PUBLICATIONS

Watson, H.R., et al., "New Compounds with the Menthol Cooling Effect", J. Soc. Cosmetic Chem., vol. 29, (1978), pp. 185-200.

Wei, E. T., et al., "AG-3-5: A Chemical Producing Sensations of Cold", J. Pharm. Pharmacol., vol. 35, (1983), pp. 110-112.

Zuker, C.S., "A Cool Ion Channel", Nature, vol. 416, (2002), pp. 27-28.

Yesilada Akgul, et al. "3,4-Dimethoxycinnamic acid tertiary amides: synthesis and evaluation of antiinflammatory and analgesic activities", Farmaco, Societa Chimica Italiana, Pavia, IT, Bd. 51, Nr. 8-9, Jan. 1, 1996, Seiten 595-599, XP008136702, ISSN: 0014-827X.

Doherty Elizabeth M., et al., "Discovery of potent, orally available vanilloid receptor-1 antagonists. Structure-activity relationship of N-aryl cinnamides", Journal of Medicinal Chemistry, American Chemical Society, Bd. 48, Nr. 1, Jan. 13, 2005, Seiten 71-90, XP002408838, ISSN: 0022-2623, DOI: DOI:10.1021/JM049485I.

Youval Shvo, et al.,"Chemical Shift Nonequivalence of Diastereotopic Protons Due to Restricted Rotation around Aryl-Nitrogen Bonds in Substituted Amides", Journal of the American Chemical Society, 89:19. Sep. 13, 1967.

European Examination Report, European Application No. 10787717.7.

German Examination Report, German Application No. 10 2010 002 558.5.

International Search Report for PCT Application No. PCT/EP2010/067936, issued May 30, 2011.

\* cited by examiner

Fig. 1a

```
ORIGIN
    1 aagaaaatcc tgcttgacaa aaaccgtcac ttaggaaaag atgtcctttc gggcagccag
   61 gctcagcatg aggaacagaa ggaatgacac tctggacagc acccggaccc tgtactccag
  121 cgcgtctcgg agcacagact tgtcttacag tgaaagcgac ttggtgaatt ttattcaagc
  181 aaattttaag aaacgagaat gtgtcttctt taccaaagat tccaaggcca cggagaatgt
  241 gtgcaagtgt ggctatgccc agagccagca catggaaggc acccagatca accaaagtga
  301 gaaatggaac tacaagaaac acaccaagga atttcctacc gacgcctttg gggatattca
  361 gtttgagaca ctggggaaga aagggaagta tatacgtctg tcctgcgaca cggacgcgga
  421 aatcctttac gagctgctga cccagcactg gcacctgaaa cacccaacc tggtcatttc
  481 tgtgaccggg ggcgccaaga acttcgccct gaagccgcgc atgcgcaaga tcttcagccg
  541 gctcatctac atcgcgcagt ccaaaggtgc ttggattctc acgggaggca cccattatgg
  601 cctgatgaag tacatcgggg aggtggtgag agataacacc atcagcagga gttcagagga
  661 gaatattgtg ccattggca tagcagcttg gggcatggtc tccaaccggg cacccctcat
  721 caggaattgc gatgctgagg gctattttt agcccagtac cttatggatg acttcacaag
  781 agatccactg tatatcctgg acaacaacca cacacatttg ctgctcgtgg acaatggctg
  841 tcatggacat cccactgtcg aagcaaagct ccggaatcag ctagagaagt atatctctga
  901 gcgcactatt caagattcca actatggtgg caagatcccc attgtgtgtt ttgcccaagg
  961 aggtggaaaa gagactttga agccatcaa tacctccatc aaaaataaaa ttccttgtgt
 1021 ggtggtggaa ggctcgggcc agatcgctga tgtgatcgct agcctggtgg aggtggagga
 1081 tgccctgaca tcttctgccg tcaaggagaa gctggtgcgc tttttacccc gcacggtgtc
 1141 ccggctgcct gaggaggaga ctgagagttg atcaaatgg ctcaaagaaa ttctcgaatg
 1201 ttctcaccta ttaacagtta ttaaaatgga agaagctggg gatgaaattg tgagcaatgc
 1261 catctcctac gctctataca aagccttcag caccagtgag caagacaagg ataactggaa
 1321 tgggcagctg aagcttctgc tggagtggaa ccagctggac ttagccaatg atgagatttt
 1381 caccaatgac cgccgatggg agtctgctga ccttcaagaa gtcatgttta cggctctcat
 1441 aaaggacaga cccaagtttg tccgcctctt tctggagaat ggcttgaacc tacggaagtt
 1501 tctcacccat gatgtcctca ctgaactctt ctccaaccac ttcagcacgc ttgtgtaccg
 1561 gaatctgcag atcgccaaga attcctataa tgatgccctc ctcacgtttg tctgaaaact
 1621 ggttgcgaac ttccgaagag gcttccggaa ggaagacaga aatggccggg acgagatgga
 1681 catagaactc cacgacgtgt ctcctattac tcggcacccc ctgcaagctc tcttcatctg
 1741 ggccattctt cagaataaga aggaactctc caaagtcatt tgggagcaga ccaggggctg
 1801 cactctggca gccctgggag ccagcaagct tctgaagact ctggccaaag tgaagaacga
 1861 catcaatgct gctggggagt ccgaggagct ggctaatgag tacgagaccc gggctgttga
 1921 gctgttcact gagtgttaca gcagcgatga agacttggca gaacagctgc tggtctattc
 1981 ctgtgaagct gggggtggaa gcaactgtct ggagctggcg gtggaggcca cagaccagca
 2041 tttcatcgcc cagcctgggg tccagaattt tctttctaag caatggtatg gagagatttc
 2101 ccgagacacc aagaactgga agattatcct gtgtctgttt attatacct tggtgggctg
 2161 tggctttgta tcatttagga gaaacctgt cgacaagcac aagaagctgc tttggtacta
 2221 tgtggcgttc ttcacctccc ccttcgtggt cttctcctgg aatgtggtct tctacatcgc
 2281 cttcctcctg ctgtttgcct acgtgctgct catggatttc cattcggtgc cacaccccc
 2341 cgagctggtc ctgtactcgc tggtcttcgt cctcttctgt gatgaagtga gacagtggta
 2401 cgtaaatggg gtgaattatt ttactgacct gtggaatgtg atggacacgc tggggcttt
 2461 ttacttcata gcaggaattg tatttcggct ccactctttc aataaaagct ctttgtattc
 2521 tggacgagtc attttctgtc tggactacat tattttcact ctaagattga tccacatttt
 2581 tactgtaagc agaaacttag gacccaagat tataatgctg cagaggatgc tgatcgatgt
 2641 gttcttcttc ctgttcctct ttgcggtgtg gatggtggcc tttggcgtgg ccaggcaagg
 2701 gatccttagg cagaatgagc agcgctggag gtggatattc cgttcggtca tctacgagcc
 2761 ctacctggcc atgttcggcc aggtgcccag tgacgtggat ggtaccacgt atgactttgc
 2821 ccactgcacc ttcactggga atgagtccaa gccactgtgt gtggagctgg atgagcacaa
 2881 cctgccccgg ttccccgagt ggatcaccat ccccctggtg tgcatctaca tgttatccac
 2941 caacatcctg ctggtcaacc tgctggtcgc catgtttggc tacacggtgg gcaccgtcca
 3001 ggagaacaat gaccaggtct ggaagttcca gaggtacttc ctggtgcagg agtactgcag
 3061 ccgcctcaat atccccttcc ccttcatcgt cttcgcttac ttctacatgg tggtgaagaa
 3121 gtgcttcaag tgttgctgca ggagaaaaaa catggagtct tctgtctgct gtttcaaaaa
 3181 tgaagacaat gagactctgg catgggaggg tgtcatgaag gaaaactacc ttgtcaagat
 3241 caacacaaaa gccaacgaca cctcagagga aatgaggcat cgatttagac aactggatac
```

Fig. 1a (cont.)

```
3301 aaagcttaat gatctcaagg gtcttctgaa agagattgct aataaaatca aataaaactg
3361 tatgaactct aatggagaaa aatctaatta tagcaagatc atattaagga atgctgatga
3421 acaattttgc tatcgactac taaatgagag attttcagac ccctgggtac atggtggatg
3481 attttaaatc accctagtgt gctgagacct tgagaataaa gtgtgtgatt ggtttcatac
3541 ttgaagacgg atataaagga agaatatttc ctttatgtgt ttctccagaa tggtgcctgt
3601 ttctctctgt gtctcaatgc ctgggactgg aggttgatag tttaagtgtg ttcttaccgc
3661 ctcctttttc ctttaatctt attttttgatg aacacatata taggagaaca tctatcctat
3721 gaataagaac ctggtcatgc tttactcctg tattgttatt ttgttcattt ccaattgatt
3781 ctctacttttt cccttttttg tattatgtga ctaattagtt ggcatattgt taaaagtctc
3841 tcaaattagg ccagattcta aaacatgctg cagcaagagg accccgctct cttcaggaaa
3901 agtgttttca tttctcagga tgcttcttac ctgtcagagg aggtgacaag gcagtctctt
3961 gctctcttgg actcaccagg ctcctattga aggaaccacc cccattccta aatatgtgaa
4021 aagtcgccca aaatgcaacc ttgaaaggca ctactgactt tgttcttatt ggatactcct
4081 cttattattt ttccattaaa aataatagct ggctattata gaaaatttag accatacaga
4141 gatgtagaaa gaacataaat tgtccccatt accttaaggt aatcactgct aacaatttct
4201 ggatggtttt tcaagtctat ttttttttcta tgtatgtctc aattctcttt caaaatttta
4261 cagaatgtta tcatactaca tatatacttt ttatgtaagc ttttttcactt agtatttttat
4321 caaatatgtt tttattatat tcatagcctt cttaaacatt atatcaataa ttgcataata
4381 ggcaacctct agcgattacc ataatttttgc tcattgaagg ctatctccag ttgatcattg
4441 ggatgagcat ctttgtgcat gaatcctatt gctgtatttg ggaaaatttt ccaaggttag
4501 attccaataa atatctattt attattaaat attaaaatat ctatttatta ttaaaaccat
4561 ttataaggct ttttcataaa tgtatagcaa ataggaatta ttaacttgag cataagatat
4621 gagatacatg aacctgaact attaaaataa aatattatat ttaaccctta gtttaagaag
4681 aagtcaatat gcttatttaa atattatgga tggtgggcag atcacttgag gtcaggagtt
4741 cgagaccagc ctggccaaca tggcaaaacc acatctctac taaaaataaa aaaattagct
4801 gggtgtggtg gtgcactcct gtaatcccag ctactcagaa ggctgaggta caagaattgc
4861 tggaacctgg gaggcggagg ttgcagtgaa ccaagattgc accactgcac tccagccggg
4921 gtgacagagt gagactccga ctgaaaataa ataaataaat aaataaataa ataaataaat
4981 attatggatg gtgaagggaa tggtatagaa ttggagagat tatcttactg aacacctgta
5041 gtcccagctt tctctggaag tggtcgtatt tgagcaggat gtgcacaagg caattgaaat
5101 gcccataatt agtttctcag ctttgaatac actataaact cactggctga aggaggaaat
5161 tttagaagga agctactaaa agatctaatt tgaaaaacta caaagcatt aactaaaaaa
5221 gtttattttc cttttgtctg ggcagtagtg aaaataacta ctcacaacat tcactatgtt
5281 tgcaaggaat taacacaaat aaaagatgcc ttttactta aacaccaaga cagaaaactt
5341 gcccaatact gagaagcaac ttgcattaga gagggaactg ttaaatgttt tcaacccagt
5401 tcatctggtg gatgttttttg caggttactc tgagaatttt gcttatgaaa aatcattatt
5461 tttagtgtag ttcacaataa tgtattgaac atacttctaa tcaaggtgc tatgtccttg
5521 tgtatggtac taaatgtgtc ctgtgtactt tgcacaact gagaatcctg cagcttggtt
5581 taatgagtgt gttcatgaaa taaataatgg aggaattgtc a
```

(SEQ ID NO: 1)

Fig. 1b

/translation="MSFRAARLSMRNRRNDTLDSTRTLYSSASRSTDLSYSESDLVNF
IQANFKKRECVFFTKDSKATENVCKCGYAQSQHMEGTQINQSEKWNYKKHTKEFPTDA
FGDIQFETLGKKGKYIRLSCDTDAEILYELLTQHWHLKTPNLVISVTGGAKNFALKPR
MRKIFSRLIYIAQSKGAWILTGGTHYGLMKYIGEVVRDNTISRSSEENIVAIGIAAWG
MVSNRDTLIRNCDAEGYFLAQYLMDDFTRDPLYILDNNHTHLLLVDNGCHGHPTVEAK
LRNQLEKYISERTIQDSNYGGKIPIVCFAQGGGKETLKAINTSIKNKIPCVVVEGSGQ
IADVIASLVEVEDALTSSAVKEKLVRFLPRTVSRLPEEETESWIKWLKEILECSHLLT
VIKMEEAGDEIVSNAISYALYKAFSTSEQDKDNWNGQLKLLLEWNQLDLANDEIFTND
RRWESADLQEVMFTALIKDRPKFVRLFLENGLNLRKFLTHDVLTELFSNHFSTLVYRN
LQIAKNSYNDALLTFVWKLVANFRRGFRKEDRNGRDEMDIELHDVSPITRHPLQALFI
WAILQNKKELSKVIWEQTRGCTLAALGASKLLKTLAKVKNDINAAGESEELANEYETR
AVELFTECYSSDEDLAEQLLVYSCEAWGGSNCLELAVEATDQHFIAQPGVQNFLSKQW
YGEISRDTKNWKIILCLFIIPLVGCGFVSFRKKPVDKHKKLLWYYVAFFTSPFVVFSW
NVVFYIAFLLLFAYVLLMDFHSVPHPPELVLYSLVFVLFCDEVRQWYVNGVNYFTDLW
NVMDTLGLFYFIAGIVFRLHSSNKSSLYSGRVIFCLDYIIFTLRLIHIFTVSRNLGPK
IIMLQRMLIDVFFFLFLFAVWMVAFGVARQGILRQNEQRWRWIFRSVIYEPYLAMFGQ
VPSDVDGTTYDFAHCTFTGNESKPLCVELDEHNLPRFPEWITIPLVCIYMLSTNILLV
NLLVAMFGYTVGTVQENNDQVWKFQRYFLVQEYCSRLNIPFPFIVFAYFYMVVKKCFK
CCCKEKNMESSVCCFKNEDNETLAWEGVMKENYLVKINTKANDTSEEMRHRFRQLDTK
LNDLKGLLKEIANKIK"

(SEQ ID NO: 2)

DETECTION AND USE OF LOW MOLECULAR-WEIGHT MODULATORS OF THE COLD-MENTHOL RECEPTOR TRPM8

RELATED APPLICATIONS

This application is a national stage application under 35 U.S.C. §371 of PCT/EP2009/061019, filed Aug. 26, 2009, which claims benefit of European application 08162997.4, filed Aug. 26, 2008.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13111-00165_ST25.txt. The size of the text file is 17 kb, and the text file was created on Feb. 23, 2011.

The invention relates to new types of modulators of the cold menthol receptor TRPM8, methods for modulating the TRPM8 receptor using these modulators; the use of the modulators for inducing a sensation of coldness; and also the articles and compositions produced using these modulators.

BACKGROUND OF THE INVENTION

The cold menthol receptor TRPM8 (also referred to as Cold Membrane Receptor (CMR)1) belongs to the family of the "Transient Receptor Potential Ion Channels", is specifically expressed in a special group of neurons and, in the cell membrane, forms pores (in each case 4 units combine to give a tetramer), which selectively allow $Ca^{2+}$ ions to pass. The protein has 6 transmembrane domains and a cytoplasmatic C and N terminus. Low temperatures (preferably 10-25° C.) stimulate this receptor, resulting in a signal transduction which is interpreted by the nervous system as a sensation of coldness. The receptor was described for the first time in 2002 as cold receptor in a number of publications (Peier A M et al, A TRP channel that senses cold stimuli and menthol. Cell. 2002 Mar. 8; 108(5):705-15; McKemy D D et al. Identification of a cold receptor reveals a general role for TRP channels in thermosensation. Nature. 2002 Mar. 7; 416 (6876): 52-8; Zuker C S. Neurobiology: a cool ion channel. Nature. 2002 Mar. 7; 416 (6876): 27-8).

Cooling compounds, such as e.g. menthol, have for a long time played an important role in the flavorings and fragrance industry in order to produce an association with freshness and cleanliness. For the compound menthol, it has been shown that it acts as a natural modulator of the receptor TRPM8 (McKemy D. D., *Molecular Pain* 1, 2005, 16; McKemy D. D., *Nature* 416, 2002, 52-58; Peier A. M., Cell 108, 2002, 705-715; Dhaka A., *Annu. Rev. Neurosci.* 29, 2006, 135-161). By applying menthol, TRPM8 is activated, which brings about a $Ca^{2+}$ influx into the cold-sensitive neurons. The electrical signal produced as a result is ultimately perceived as a sensation of coldness. Elevated menthol concentrations lead to irritation and an anesthetic effect. Moreover, various publications have described menthol derivatives with a similar effect (British Patent 1971#1315761; Watson H. R., *J. Soc. Cosmet. Chem.* 29, 1978, 185-200; Furrer S. M., *Chem. Percept.* 1, 2008, 119-126). There are also individual compounds, structurally unrelated to menthol, which bring about a significant TRPM8 modulation, such as e.g. Icilin (Wei E. T., *J. Pharm. Pharmacol.* 35, 1983, 110-112; WO 2004/026840), WS-23 or compounds listed in the patent application WO 2007/019719.

Further effects of substances which modulate the TRPM8 receptor and/or its insect analogs are a repellent effect on insects (WO 2002/015692; WO 2004/000023, US 2004/0028714), and also activity in antitumor therapy (e.g. an influencing of prostate tumors), activity in the treatment of inflammatory pain/hyperalgesia and an effect as TRPM8 antagonists in the treatment of bladder syndrome or overactive bladder (Beck B. *Cell Calcium*, 41, 2007, 285-294; Levine J. D. *Biochim. Biophys. Acta, Mol. Basis Dis.* 1772, 2007, 989-1003; Mukerji G., *BMC Urology* 6, 2006, 6; US 2003/0207904; US 2005/6893626, Dissertation Behrendt H. J. 2004, Universität Bochum; Lashinger E. S. R. *Am. J. Physiol. Renal Physiol.* Am J Physiol Renal Physiol. 2008 Jun. 18. [Epub ahead of print]; PMID: 18562636).

However, many of the TRPM8 modulators found hitherto have deficiencies with regard to strength of effect, duration of effect, skin/mucosa irritation, odor, taste, solubility and/or volatility.

SUMMARY OF THE INVENTION

It was therefore an object of the present invention to identify novel substances, which lead to a modulation of the TRPM8 receptor, which can be used as alternatives to the modulators known hitherto. Such compounds should in particular also be suitable for applications in the field of cosmetics (e.g. hair care, skin care, oral care), nutrition (feed/food), textiles, OTC products (e.g. burn ointment), pharmaceuticals (e.g. tumor treatment, bladder weakness), packagings or as insecticide or repellent.

BRIEF DESCRIPTION OF THE DRAWINGS

FIG. 1 shows (FIG. 1a) the mRNA sequence (SEQ ID NO: 1) and (FIG. 1b) the amino acid sequence (SEQ ID NO: 2) derived therefrom of the hTRPM8 receptor according to sequence databank entry NM_024080.

DETAILED DESCRIPTION OF THE INVENTION

1. Definition of General Terms

Figure 2:
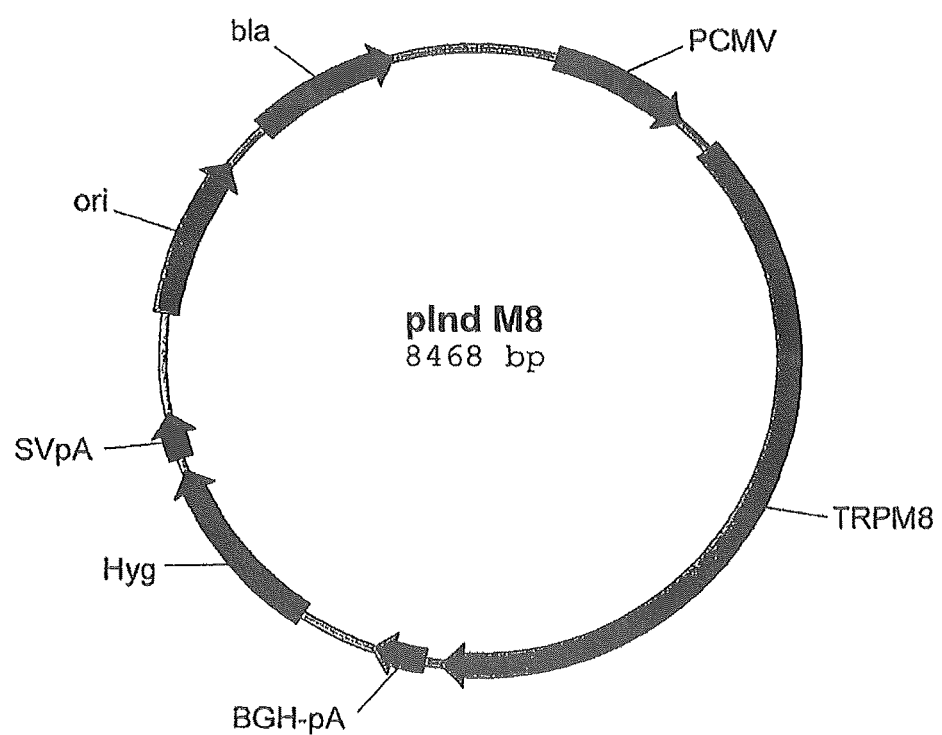
FIG. 2 shows the vector map of the plasmid plnd_M8 coding with hTRPM8, which has been used for the transfection of HEK293 cells.

In the literature there are various synonyms for "TRPM8": TRPP8, LTRPC6, CMR1, MGC2849, transient receptor potential cation channel subfamily M member 8. Within the context of the present invention, all names are encompassed. Also encompassed are all functional modifications of the receptor, such as, in particular, splice variants, isoforms, such as e.g. TRPM8 CRA_a, TRPM8 CRA_b and all analogous receptors from various organisms, such as human, mouse, rat. The nucleotide and amino acid sequences of the various receptors are known per se and listed in sequence databases. Thus, e.g. the sequence information for hTRPM8 is entered under the number NM_024080.

Within the context of the invention, a "modulator" is a compound which can act as agonist and/or antagonist of the TRPM8 receptor in vivo and/or in vitro.

Suitable modulators here can act either only as antagonist or agonist or both as antagonist and also as agonist. Here, in particular an agonistic or an antagonistic effect can be established depending on the particular modulator concentration selected.

Here, an "agonist" is a compound which mediates an activation of the TRPM8 receptor, thus induces a $Ca^{2+}$ ingress into the cold-sensitive neurons and thereby mediates a sensation of coldness. By contrast, an "antagonist" is a compound which can counteract this activation of the TRPM8 receptor.

The mediators according to the invention can exert their effect by binding reversibly or irreversibly, specifically or nonspecifically to a TRPM8 receptor molecule. Usually, the binding takes place noncovalently via ionic and/or nonionic, such as e.g. hydrophobic, interactions with the receptor molecule. Here, "specific" encompasses both exclusive interaction with one or more different TRPM8 receptor molecules (such as e.g. TRPM8 molecules of different origin or various isoforms). By contrast, "nonspecific" is an interaction of the modulator with a plurality of various receptor molecules of different function and/or sequence but where, as a consequence, a desired agonistic and/or antagonistic modulation (as described above) of the TRPM8 receptor can be established.

2. Preferred Embodiments

The invention relates firstly to a method for the in-vitro or in-vivo modulation of the cold menthol receptor TRPM8, in particular of the human TRPM8 receptor, where the receptor is brought into contact with at least one compound which is selected from polynuclear organic compounds which, in a cellular activity test, in particular under standard conditions, using cells which recombinantly express the human TRPM8 receptor, modulate the permeability of these cells for $Ca^{2+}$ ions.

In this connection, "standard conditions" is understood as meaning an activity test carried out with HEK293 cells which have been transformed with human TRPM8 and loaded with calcium-sensitive dye (such as e.g. Fluo-4AM, i.e. fluo-4-acetoxymethyl ester), subsequent addition of the test compound and detection of the color change, the experimental procedure taking place at 37° C.; as described e.g. example 3 below, or in Behrendt et al. (2004) loc. cit.).

In particular, the modulating compound here comprises at least two 4- to 7-membered rings which, independently of one another, are carbocyclic or heterocyclic, monocyclic or polycyclic, and where at least two of these rings may be optionally condensed or spiro-linked. Other nonlimiting examples of suitable ring linkages comprise chemical single bonds between ring carbon atoms and/or ring heteroatoms, via 2 to 6-membered carbon bridging groups, where individual carbon atoms may be replaced by heteroatoms, such as N, O or S. Moreover, the ring groups and bridging groups may optionally carry substituents which are selected from keto groups, —OH, —SH, —CN, —NO$_2$, —C$_{1-6}$-alkyl, or C$_{2-4}$-alkenyl, where, in the alkyl or alkenyl groups, one or more H atoms may be replaced by halogen, such as F, Cl, Br or I.

Carbocyclic rings comprise here 4, 5, 6 or 7 carbon atoms; besides the ring carbon atoms, heterocyclic rings comprise 1 to 3 identical or different ring heteroatoms, such as O, N and S atoms. The rings here may be, independently of one another, saturated, mono- or polyunsaturated, such as e.g. aromatic rings.

The modulator used according to the invention have an agonistic or antagonistic effect here on the cellular $Ca^{2+}$ ion permeability. In particular, the modulator is at least one compound selected from compounds of the following formulae 1 to 19 according to table 1 below.

TABLE 1

Modulators according to the invention

1

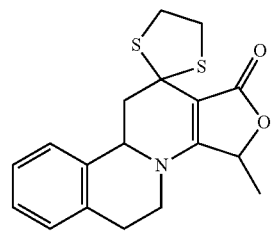 [SMILES: CC1OC(=O)C2=C1N1CCc3ccccc3C1CC21SCCS1]

2

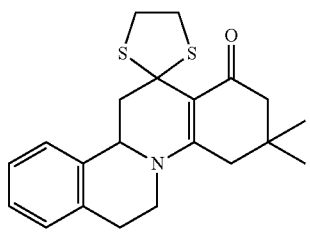 [SMILES: CC1(C)CC(=O)C2=C(C1)N1CCc3ccccc3C1CC21SCCS1]

3

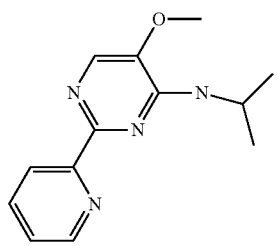 [SMILES: COc1cnc(-c2ccccn2)nc1NC(C)C]

4

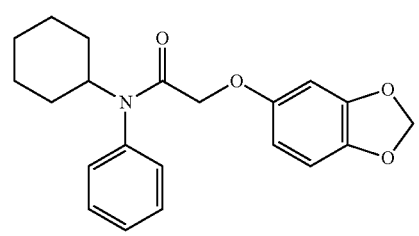 [SMILES: O=C(COc1ccc2c(c1)OCO2)N(c1ccccc1)C1CCCCC1]

5

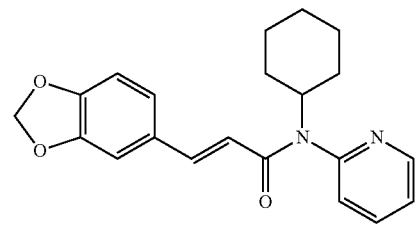 [SMILES: O=C(/C=C/c1ccc2c(c1)OCO2)N(c1ccccn1)C1CCCCC1]

6

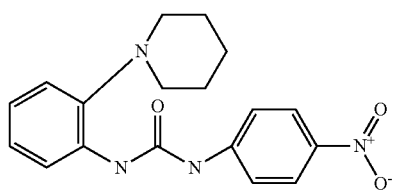 [SMILES: O=C(Nc1ccc([N+](=O)[O-])cc1)Nc1ccccc1N1CCCCC1]

TABLE 1-continued

Modulators according to the invention

| # | Structure |
|---|---|
| 7 | (structure) |
| 8 | (structure) |
| 9 | (structure) |
| 10 | (structure) |
| 11 | (structure) |
| 12 | (structure) |
| 13 | (structure) |
| 14 | (structure) |
| 15 | (structure) |
| 16 | (structure) |
| 17 | (structure) |

TABLE 1-continued

Modulators according to the invention

18

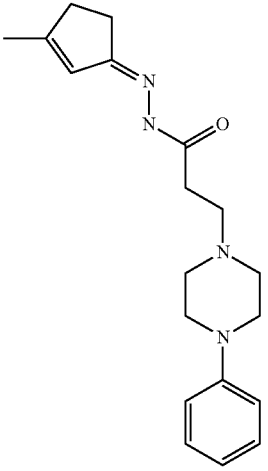

19

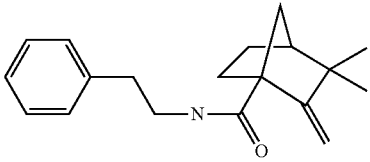

where the compound may be present in chemically pure or enriched form, as individual stereoisomer or in the form of stereoisomer mixtures. Furthermore, the compounds can be present uncharged or in the form of their salts, such as e.g. as acid addition salt. Functional groups may optionally be replaced by equivalent chemical groups; fluorine atoms may thus be replaced e.g. by other halogen atoms, such as Cl, Br or I; oxygen atoms (such as e.g. ether groups) may be replaced by corresponding sulfur groups, and vice versa; keto groups may be replaced by corresponding thionyl groups. The compounds specified above are chemical substances known per se which are either commercially available or are obtainable using customary organic synthesis methods.

Thus, the following are known for example:
Compound 1 under CAS number: 99602-94-5 (3R-cis form)
Compound 2 under CAS number: 165753-08-2
Compound 3 under CAS number: 338771-57-6
Compound 4 under CAS number: 878942-21-3
Compound 5 under CAS number: 748783-13-3

The modified forms or derivatives are also referred to as functional analogs or functionally equivalent compounds, if they furthermore exhibit the desired biological activity (receptor TRPM8 modulation).

Furthermore, particularly derivatives which permit a coupling of the specifically disclosed substances to solid carriers are also encompassed within the context of the invention; a large selection of corresponding linker/spacer groups is known to the person skilled in the art. The derivatization can take place here prior to the coupling to a solid phase or only as a result of the coupling.

The invention further relates to the use of a modulator, in particular agonists, for the TRPM8 receptor, where the modulator is as defined above, for inducing a sensation of coldness, in particular topically, i.e. cutaneously or orally, in humans and/or animals. An "induction of a sensation of coldness" is present when the compound in the cellular activity test described above exhibits an agonistic effect on hTRPM8.

The invention further relates to the use of a modulator for the TRPM8 receptor, where the modulator is as defined above, as active constituent of a pharmaceutical composition.

The invention further relates to the use of a modulator for the TRPM8 receptor, where the modulator is as defined above, for the treatment of prostate carcinomas, for the treatment of bladder weakness or in pain therapy.

The invention further relates to the use of a modulator for the TRPM8 receptor, where the modulator is as defined above, as insect repellent or insecticide.

The invention further relates to the use of a modulator for the TRPM8 receptor, where the modulator is as defined above, for inducing a sensation of coldness in packagings (e.g. made of paper or plastic) in a very wide variety of processing forms (such as e.g. fibers, fabrics, moldings), where the sensation of coldness becomes noticeable in particular upon contact with the packaging material. In this connection, the substances can be associated in very diverse ways with the packaging material: e.g. by spin-coating, imprinting, in the form of microencapsulation, direct incorporation into the packaging material (e.g. extruding), covalent coupling of suitable derivatives of the modulators (via suitable spacer/linker groups, with the help of which the molecule is reversibly or irreversibly bonded to the packaging material). Suitable methods are known to the person skilled in the art.

The invention further relates to the use of a modulator for the TRPM8 receptor, where the modulator is as defined above, for inducing a sensation of coldness in textiles. In this connection, the substances can be associated in very diverse ways with the textile: e.g. by spin-coating, imprinting, in the form of microencapsulation, direct incorporation into the textile material (e.g. extruding), covalent coupling of suitable derivatives of the modulators (via suitable spacer/linker groups, with the help of which the molecule is reversibly or irreversibly bonded to the packaging material). Suitable methods are known to the person skilled in the art.

The invention further relates to substances per se according to the above definition for use as mediator, in particular agonists and/or antagonists, of the TRPM8 receptor.

The invention further relates to compositions comprising at least one compound according to the above definition. In particular, such compositions are selected from
a) pharmaceutical compositions, such as antitumor compositions, compositions for the treatment of diseases of the bladder, painkillers;
b) foods, such as ice cream, mousse, cream, beverages, confectionery,
c) mouthcare compositions, such as toothpaste, mouthwash, chewing gum, breath fresheners
d) skincare or haircare compositions, such as suncream, sunburn cream, lotions, shampoos, plasters, mouthwash, lotions, shaving cream, conditioners, face cleansers, soaps, bath oils and bath foams, antiperspirants, deodorants,
e) insect repellents, insecticides.

Besides constituents customary in each case for the particular composition, such compositions comprise an effective amount of at least one modulator according to the invention. In this connection, "effective" means a concentration of the modulator which suffices to bring about the desired effect, such as e.g. pharmacological effect, or sensory effect, such as the olfactory effect of coldness, upon application of the composition (e.g. application to the skin).

Optionally, the compounds according to the invention can be combined with further known active ingredients, in particular also those with a comparable effect. For example, these can be combined with known cooling compounds, such as e.g. menthol, menthone, N-ethyl-p-menthanecarboxamide (WS-3), N-2,3-trimethyl-2-isopropylbutanamide (WS-23), menthyl lactate (FRESCOLAT® ML), menthone glycerol acetal (FRESCOLAT® MGA), monomenthyl succinate (PHYSCOOL®), monomenthyl glutarate, O-menthylglycerol, menthyl N,N-dimethylsuccinamate.

The invention furthermore relates to textile products, such as e.g. shirts, trousers, socks, towels, finished (in particular on the surface) with at least one compound according to the above definition.

The invention furthermore relates to packaging materials which are associated with at least one compound according to the above definition.

The invention will now be described with reference to the following nonlimiting working examples.

EXPERIMENTAL SECTION

Example 1

Cloning of Human TRPM8

The starting point for the cloning of the human TRPM8 receptor is an LnCaP cDNA library. This is, for example, commercially available (e.g. BioChain, Hayward, USA) or can be produced from the androgen-sensitive human prostate adenocarcinoma cell line LnCaP (e.g. ATCC, CRL1740 or ECACC, 89110211) using standard kits.

The coding TRPM8 sequence (cf. FIG. 1A) can be PCR-amplified and cloned using standard methods. The human TRPM8 gene isolated in this way was used for producing the plasmid plnd_M8, the construction of which is illustrated by the plasmid map according to FIG. 2.

Alternatively to this, the TRPM8 gene can also be produced synthetically.

Example 2

Generation of the HEK293 Test Cells

As test cell system, HEK293 cell line stably transfected with the human TRPM8 DNA (cf. above plasmid plnd-M8) are produced. Preference here is given to HEK293 which offers the option, via the introduced plasmid, of inducing the TRPM8 expression by means of tetracycline.

Methods for producing suitable test cell systems are known to the person skilled in the art. For example, the details of the preparation of the cells used according to the invention can be found in Behrendt H. J. et al., *Br. J. Pharmacol.* 141, 2004, 737-745 or the dissertation by Behrendt "Vergleichende funktionale Untersuchungen des Hitze-Capsaicin-Rezeptors (TRPV1) und des Kälte-Menthol-Rezeptors (TRPM8) in rekombinanten und nativen Zellsystemen". [Comparative functional investigations of the heat capsaicin receptor (TRPV1) and of the cold menthol receptor (TRPM8) in recombinant and native cell systems].

Reference is expressly made to the disclosure of these documents.

Example 3

Assay on TRPM8 Modulators

A test comparable with the test already described in the literature by Behrendt H. J. et al., *Br. J. Pharmacol.* 141, 2004, 737-745 is carried out. The agonization or antagonization of the receptor can be quantified by means of a $Ca^{2+}$-sensitive dye (e.g. FURA, Fluo-4 etc.). On their own, agonists bring about an increase in the $Ca^{2+}$ signal; antagonists bring about, in the presence of e.g. menthol, a reduction in the $Ca^{2+}$ signal (in each case detected via the dye Fluo-4, which has different fluorescent properties as the result of $Ca^{2+}$).

a) Test Procedure:

Firstly, a fresh culture of transformed HEK cells is prepared in a manner known per se in cell culture flasks. The test cells HEK293-TRPM8 are detached from the cell culture flasks by means of trypsin and 40 000 cells/well are sown out with 100 µl of medium in 96-well plates (Greiner #655948 poly-D-lysine-coated). To induce the receptor TRPM8, tetracycline is added to the growth medium (DMEM/HG, 10% FCS tetracycline-free, 4 mM L-glutamine, 15 µg/ml blasticidin, 100 µg/ml hygromycin B, 1 µg/ml tetracycline). On the following day, the cells are loaded with Fluo-4AM dye and the test is carried out. For this, the procedure is as follows:

addition of in each case 100 µl/well of dye solution Ca-4 kit (RB 141, Molecular Devices) to in each case 100 µl of medium (DMEM/HG, 10% FCS tetracycline-free, 4 mM L-glutamine, 15 µg/ml blasticidin, 100 µg/ml hygromycin B, 1 µg/ml tetracycline)

incubation in the hatching cabinet, 30 minutes/37° C./5% $CO_2$, 30 minutes/RT preparation of the test substances (various concentrations in 200 µl of HBSS buffer), and also of positive controls (various concentrations of menthol, icilin and ionomycin in 200 µl of HBSS buffer) and negative controls (only 200 µl of HBSS buffer)

addition of the test substances in amounts of 50 µl/well and measurement of the change in fluorescence (e.g. in the assay instrument FLIPR, Molecular Devices or NovoStar, BMG) at 485 nm excitation, 520 nm emission, and evaluation of the effectiveness of the various substances/concentrations and determination of the EC50 values.

The test substances are used in the assay in triplicate in concentrations of 0.1-200 µM. Normally, the compounds are kept ready in DMSO solutions and are diluted down to a maximum DMSO concentration of 2% for the assay.

b) Test Result

The EC50 values determined for modulators according to the invention are summarized in table 2 below

TABLE 2

Activity of test substances on the human receptor TRPM8

| # | Activity TRPM8 EC50 |
|---|---|
| 1 | 0.4 |
| 2 | 2 |
| 3 | 2 |
| 4 | 2.5 |
| 5 | 2.5 |
| 6 | 3.5 |
| 7 | 4 |
| 8 | 5 |
| 9 | 10 |
| 10 | 10 |
| 11 | 10 |
| 12 | 10 |
| 13 | 10 |
| 14 | 20 |
| 15 | 20 |
| 16 | 25 |
| 17 | 50 |
| 18 | 100 |
| 19 | 100 |

The evaluation surprisingly reveals that, according to the invention, it was possible for the first time to prepare agonists of TRPM8 which differ significantly in structural terms from agonists known hitherto, such as (−) menthol, icilin and other modulators described by Behrendt H. J. et al., in *Br. J. Pharmacol.* 141, 2004, 737-745 (cf. table 1 therein), and, moreover, in some cases exhibit better activities than (−) menthol, or are as comparably effective as icilin.

Example 4

Preparation of Mouthwash

A mouthwash of the following composition is prepared:

| Ethanol 95% | 177 ml |
|---|---|
| Sorbitol 70% | 250 g |
| TRPM8 agonist according to tab. 2 as 1% solution in the ethanol | 50 ml |
| Peppermint oil | 0.30 g |
| Methyl salicylate | 0.64 g |
| Eucalyptol | 0.922 g |
| Thymol | 0.639 g |
| Benzoic acid | 1.50 g |
| PLURONIC ® F127 nonionic surfactant | 5.00 g |
| Sodium saccharin | 0.60 g |
| Sodium citrate | 0.30 g |
| Citric acid | 0.10 g |
| Water | q.s. 1 liter |

To prepare a mouthwash, the above-described components are mixed together in the stated amounts.

Reference is hereby expressly made to the disclosure of the literature sources cited herein.

The invention claimed is:

1. A method for in-vitro or in-vivo modulation of cold menthol receptor TRPM8 comprising contacting the receptor with a polynuclear organic compound, wherein in a cellular activity test, the compound is a modulator of the $Ca^{2+}$ ion permeability of a cell that recombinantly expresses a human TRPM8 receptor, and wherein the modulator is selected from the group consisting of the compounds of formulae 1 to 19:

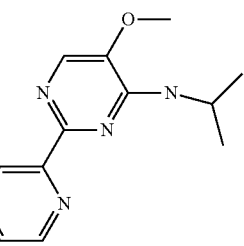

1

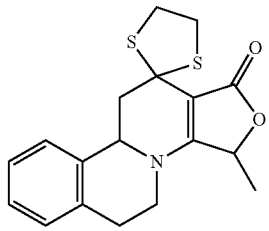

2

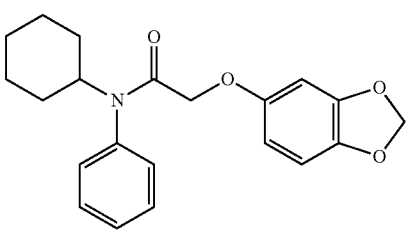

3

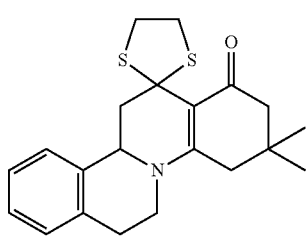

4

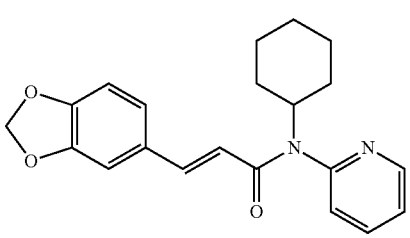

5

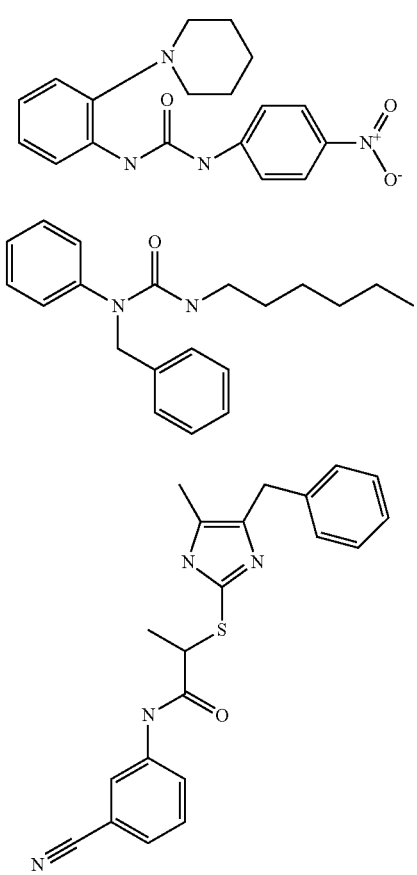
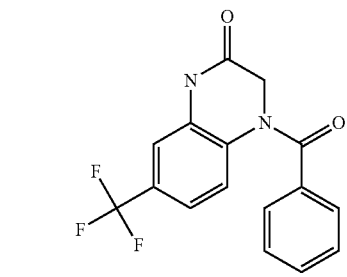 [SMILES: O=C1CN(C(=O)c2ccccc2)c2ccc(C(F)(F)F)cc2N1]
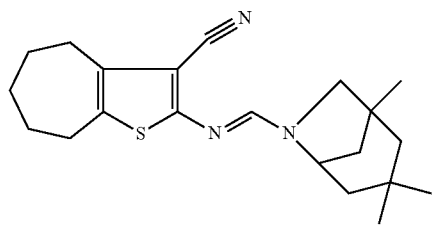
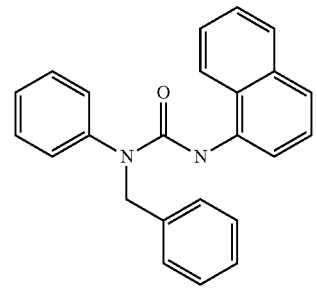 [SMILES: O=C(Nc1cccc2ccccc12)N(Cc1ccccc1)c1ccccc1]
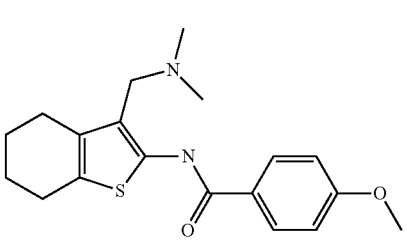 [SMILES: COc1ccc(C(=O)Nc2sc3c(c2CN(C)C)CCCC3)cc1]
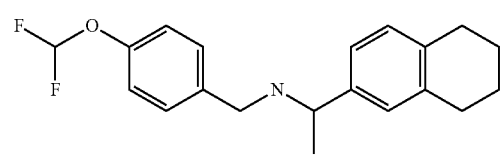 [SMILES: CC(NCc1ccc(OC(F)F)cc1)c1ccc2c(c1)CCCC2]
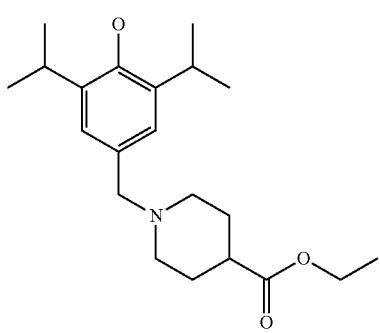 [SMILES: CCOC(=O)C1CCN(Cc2cc(C(C)C)c(O)c(C(C)C)c2)CC1]
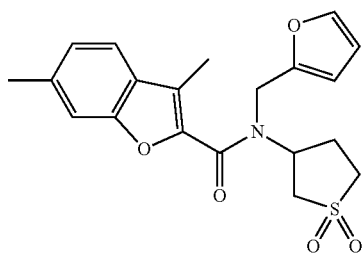 [SMILES: Cc1ccc2c(C)c(C(=O)N(Cc3ccco3)C3CCS(=O)(=O)C3)oc2c1]
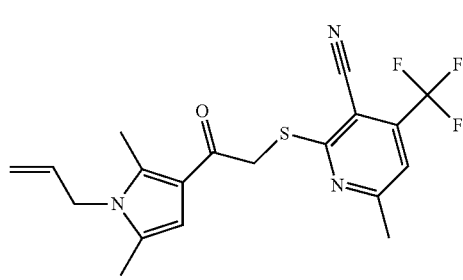
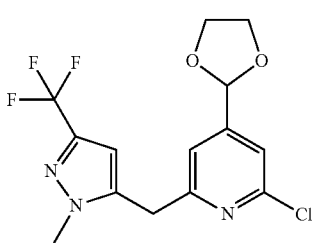

18

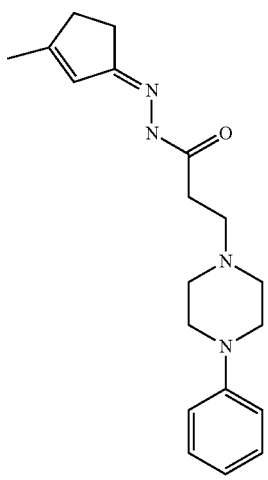 [SMILES: CC1=C/C(=N\NC(=O)CCN2CCN(c3ccccc3)CC2)CC1]

19

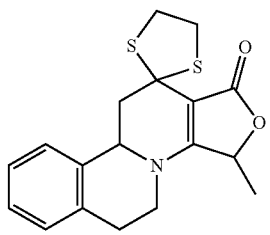

2. A method for inducing a sensation of coldness in at least one of a human or an animal, the method comprising contacting the human or animal with a polynuclear organic compound, wherein in a cellular activity test, the compound is a modulator of the Ca2+ ion permeability of a cell that recombinantly expresses a human TRPM8 receptor and wherein the modulator is selected from the group consisting of the compounds of formula 1 to 19:

1

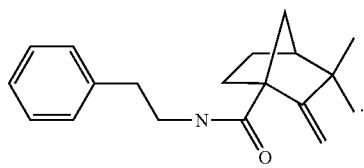

2

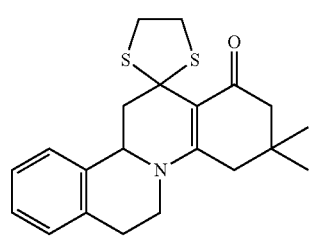

3

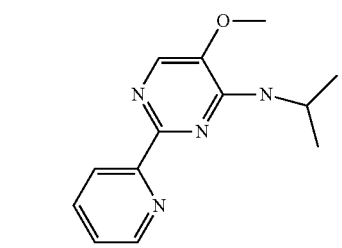

4

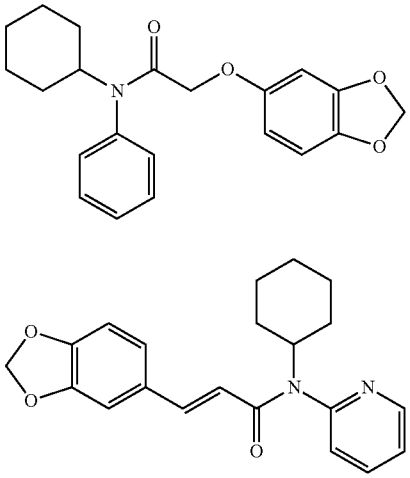

5

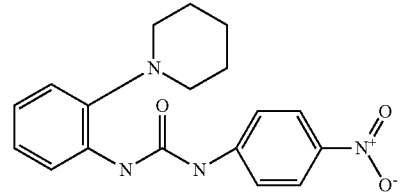

6

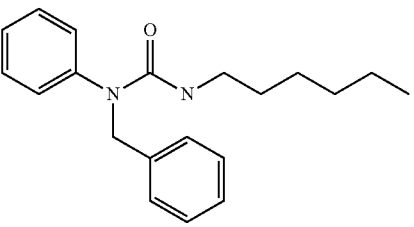

7

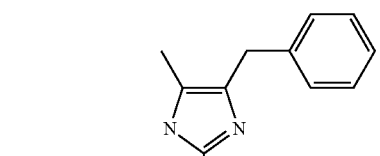

8

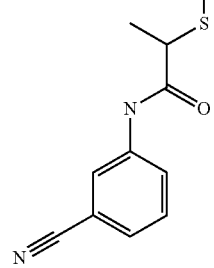

-continued
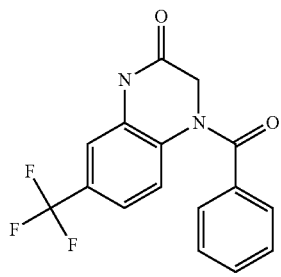
9
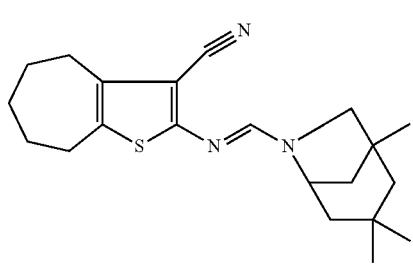
10
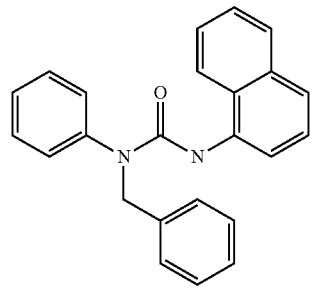
11
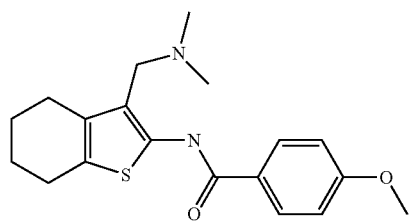
12
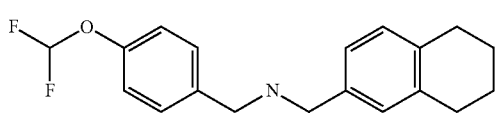
13
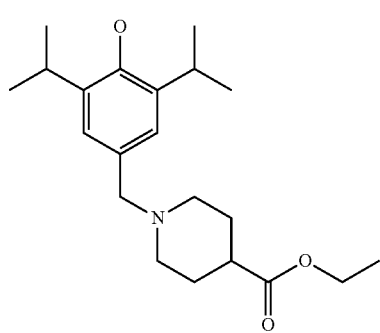
14
-continued
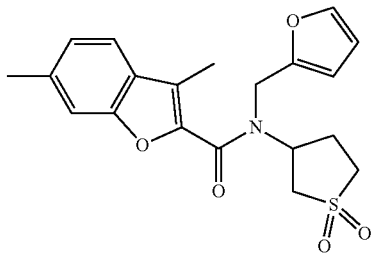
15
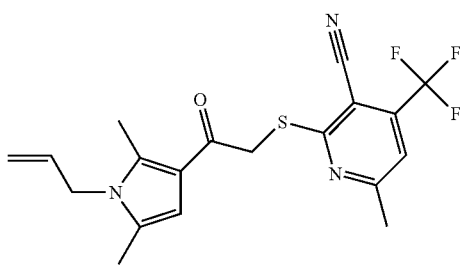
16
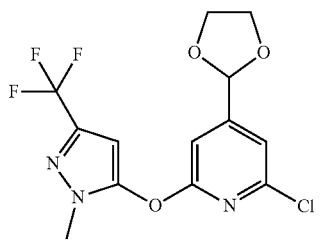
17
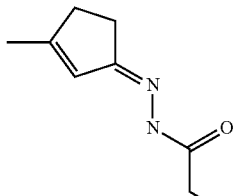
18
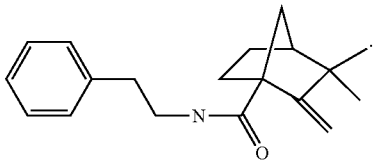
19
3. The method of claim 2, wherein the method is used in the treatment of a malady selected from the group consisting of prostate carcinoma, bladder weakness and pain.
4. A modulator for a TRPM8 receptor, wherein the modulator is selected from the compounds of formula 1 to 19:

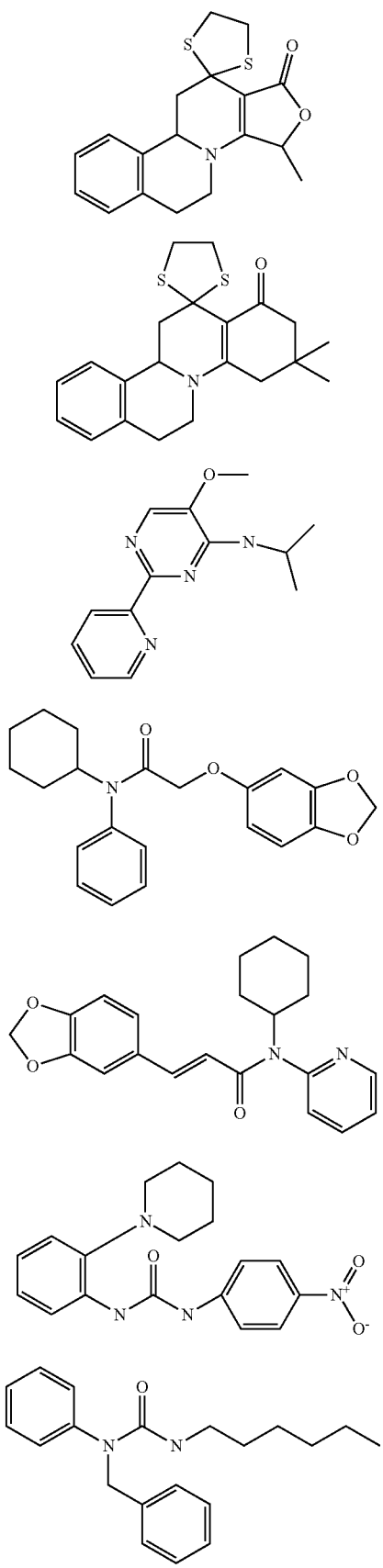
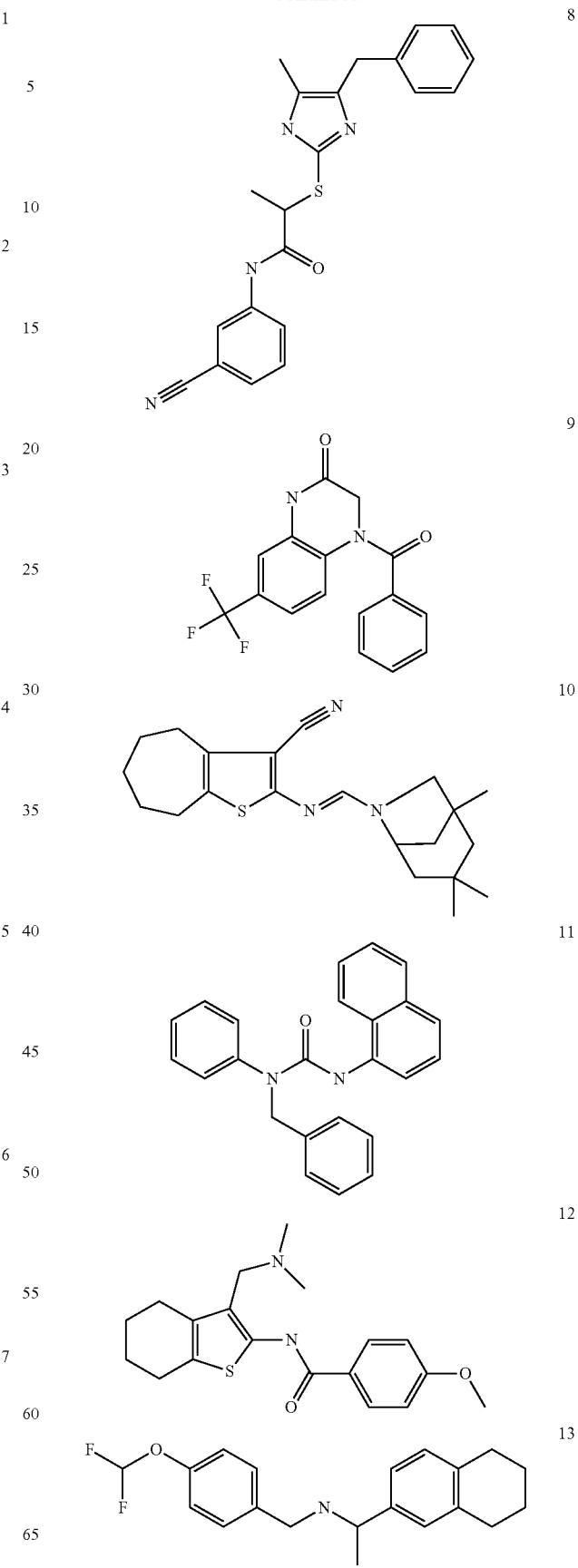

31
-continued

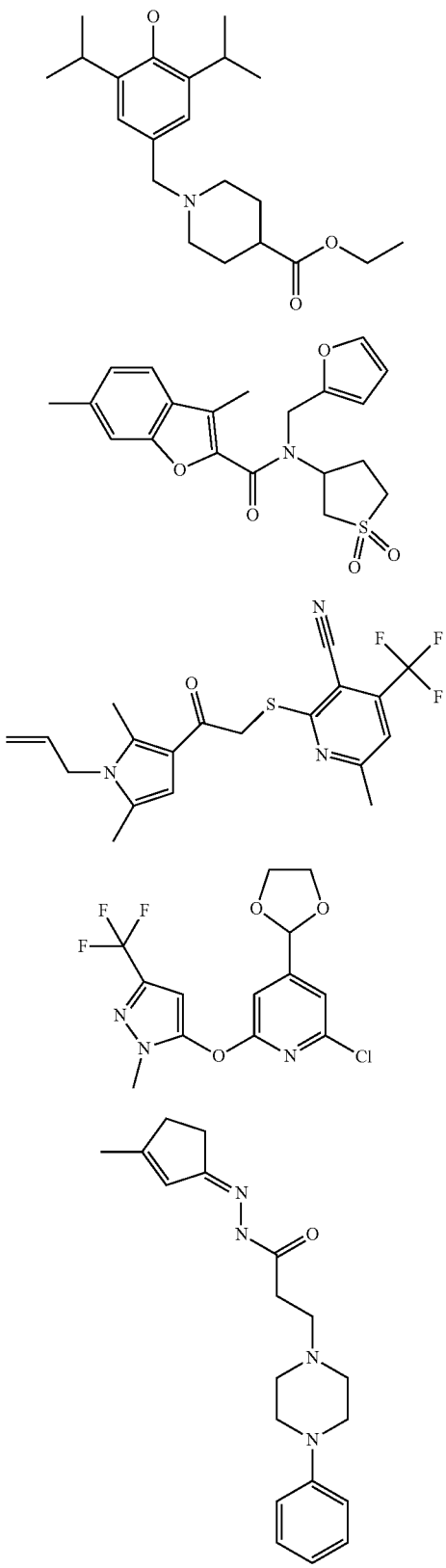

32
-continued

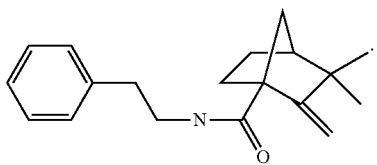

5. A method for inducing a sensation of coldness in at least one of a human or an animal comprising contacting a packaging material comprising the modulator of claim 4.

6. A method for inducing a sensation of coldness in at least one of a human or an animal comprising contacting a textile comprising the modulator of claim 4.

7. A composition comprising the modulator of claim 4, wherein the composition is selected from the group consisting of
 a. pharmaceutical compositions,
 b. foods,
 c. mouthcare compositions,
 d. skincare or haircare compositions, and
 e. insect repellents and insecticides.

8. The composition of claim 7, wherein the composition is a pharmaceutical composition.

9. The composition of claim 7, wherein the food is an ice cream, a mousse, cream, a beverage or a confection.

10. The composition of claim 7, wherein the mouthcare composition is a toothpaste, a mouthwash or a chewing gum.

11. The composition of claim 7, wherein the skincare or haircare composition is a suncream, a sunburn cream, a lotion, a shampoo or a plaster.

12. A textile product comprising the modulator of claim 4.

13. The textile product of claim 12, wherein the textile product is selected from the group consisting of shirts, trousers, socks and towels.

14. A packaging material comprising the modulator of claim 4.

15. The method of claim 1, wherein the modulator is the compound of formula 14.

16. The method of claim 1, wherein the modulator is the compound of formula 15.

17. The method of claim 1, wherein the modulator is the compound of formula 16.

18. The method of claim 1, wherein the modulator is the compound of formula 17.

19. The method of claim 1, wherein the modulator is the compound of formula 18.

20. The method of claim 1, wherein the modulator is the compound of formula 19.

* * * * *

SEQUENCE LISTING

<160> NUMBER OF SEQ ID NOS: 2

<210> SEQ ID NO 1
<211> LENGTH: 5621
<212> TYPE: DNA
<213> ORGANISM: Homo sapiens

<400> SEQUENCE: 1

```
aagaaaatcc tgcttgacaa aaaccgtcac ttaggaaaag atgtcctttc gggcagccag      60
gctcagcatg aggaacagaa ggaatgacac tctggacagc acccggaccc tgtactccag     120
cgcgtctcgg agcacagact tgtcttacag tgaaagcgac ttggtgaatt ttattcaagc     180
aaattttaag aaacgagaat gtgtcttctt taccaaagat tccaaggcca cggagaatgt     240
gtgcaagtgt ggctatgccc agagccagca catggaaggc acccagatca accaaagtga     300
gaaatggaac tacagaaaac acaccaagga atttcctacc gacgcctttg gggatattca     360
gtttgagaca ctggggaaga aagggaagta tatacgtctg tcctgcgaca cggacgcgga     420
aatcctttac gagctgctga cccagcactg gcacctgaaa acacccaacc tggtcatttc     480
tgtgaccggg ggcgccaaga acttcgccct gaagccgcgc atgcgcaaga tcttcagccg     540
gctcatctac atcgcgcagt ccaaaggtgc ttggattctc acgggaggca cccattatgg     600
cctgatgaag tacatcgggg aggtggtgag agataacacc atcagcagga gttcagagga     660
gaatattgtg gccattggca tagcagcttg gggcatggtc tccaaccggg acaccctcat     720
caggaattgc gatgctgagg gctattttt agcccagtac cttatggatg acttcacaag     780
agatccactg tatatcctgg acaacaacca cacacatttg ctgctcgtgg acaatggctg     840
tcatggacat cccactgtcg aagcaaagct ccggaatcag ctagagaagt atatctctga     900
gcgcactatt caagattcca actatggtgg caagatcccc attgtgtgtt ttgcccaagg     960
aggtggaaaa gagactttga agccatcaa tacctccatc aaaaataaaa ttccttgtgt    1020
ggtggtggaa ggctcgggcc agatcgctga tgtgatcgct agcctggtgg aggtggagga    1080
tgccctgaca tcttctgccg tcaaggagaa gctggtgcgc tttttacccc gcacggtgtc    1140
ccggctgcct gaggaggaga ctgagagttg gatcaaatgg ctcaaagaaa ttctcgaatg    1200
ttctcaccta ttaacagtta ttaaaatgga agaagctggg gatgaaattg tgagcaatgc    1260
catctcctac gctctataca aagccttcag caccagtgag caagacaagg ataactgaaa    1320
tgggcagctg aagcttctgc tggagtggaa ccagctggac ttagccaatg atgagatttt    1380
```

```
caccaatgac cgccgatggg agtctgctga ccttcaagaa gtcatgttta cggctctcat    1440
aaaggacaga cccaagtttg tccgcctctt tctggagaat ggcttgaacc tacgaagtt     1500 tctcacccat gatgtcctca ctgaactctt ctccaaccac ttcagcacgc ttgtgtaccg    1560
gaatctgcag atcgccaaga attcctataa tgatgccctc ctcacgtttg tctggaaact    1620
ggttgcgaac ttccgaagag gcttccggaa ggaagacaga aatggccggg acgagatgga    1680
catagaactc cacgacgtgt ctcctattac tcggcacccc ctgcaagctc tcttcatctg    1740
ggccattctt cagaataaga aggaactctc caaagtcatt tgggagcaga ccaggggctg    1800
cactctggca gccctgggag ccagcaagct tctgaagact ctggccaaag tgaagaacga    1860
catcaatgct gctggggagt ccgaggagct ggctaatgag tacgagaccc gggctgttga    1920
gctgttcact gagtgttaca gcagcgatga agacttggca gaacagctgc tggtctattc    1980
ctgtgaagct tggggtggaa gcaactgtct ggagctggcg gtggaggcca cagaccagca    2040
tttcatcgcc cagcctgggg tccagaattt tctttctaag caatggtatg agagatttc    2100 ccgagacacc aagaactgga agattatcct gtgtctgttt attataccct tggtgggctg    2160 tggcttttgta tcatttagga agaaacctgt cgacaagcac aagaagctgc tttggtacta    2220
tgtggcgttc ttcacctccc ccttcgtggt cttctcctgg aatgtggtct tctacatcgc    2280
cttcctcctg ctgtttgcct acgtgctgct catggatttc cattcggtgc cacaccccc     2340 cgagctggtc ctgtactcgc tggtctttgt cctcttctgt gatgaagtga cacagtggta    2400
cgtaaatggg gtgaattatt ttactgacct gtggaatgtg atggacacgc tggggctttt    2460
ttacttcata gcaggaattg tatttcggct ccactcttct aataaaagct ctttgtattc    2520
tggacgagtc attttctgtc tggactacat tatttcact ctaagattga tccacatttt    2580
tactgtaagc agaaacttag gacccaagat tataatgctg cagaggatgc tgatcgatgt    2640
gttcttcttc ctgttcctct ttgcggtgtg gatggtggcc tttggcgtgg ccaggcaagg    2700
gatccttagg cagaatgagc agcgctggag gtggatattc cgttcggtca tctacgagcc    2760
ctacctggcc atgttcggcc aggtgcccag tgacgtggat ggtaccacgt atgactttgc    2820
ccactgcacc ttcactggga atgagtccaa gccactgtgt gtggagctgg atgagcacaa    2880
cctgccccgg ttccccgagt ggatcaccat cccctggtg tgcatctaca tgttatccac    2940
caacatcctg ctggtcaacc tgctggtcgc catgtttggc tacacggtgg gcaccgtcca    3000
ggagaacaat gaccaggtct ggaagttcca gaggtacttc ctggtgcagg agtactgcag    3060
ccgcctcaat atccccttcc ccttcatcgt cttcgcttac ttctacatgg tggtgaagaa    3120
gtgcttcaag tgttgctgca aggagaaaaa catggagtct tctgtctgct gtttcaaaaa    3180
tgaagacaat gagactctgg catgggaggg tgtcatgaag gaaaactacc ttgtcaagat    3240
caacacaaaa gccaacgaca cctcagagga aatgaggcat cgatttagac aactggatac    3300
aaagcttaat gatctcaagg gtcttctgaa agagattgct aataaaatca ataaaactg     3360 tatgaactct aatggagaaa aatctaatta tagcaagatc atattaagga atgctgatga    3420
acaattttgc tatcgactac taaatgagag attttcagac ccctgggtac atggtggatg    3480 atttaaatc accctagtgt gctgagacct tgagaataaa gtgtgtgatt ggttcatac     3540 ttgaagacgg atataaagga agaatatttc ctttatgtgt ttctccagaa tggtgcctgt    3600
ttctctctgt gtctcaatgc ctgggactgg aggttgatag tttaagtgtg ttcttaccgc    3660 ctccttttc ctttaatctt attttttgatg aacacatata taggagaaca tctatcctat    3720
gaataagaac ctggtcatgc tttactcctg tattgttatt ttgttcatt ccaattgatt     3780
```

-continued

```
ctctactttt ccctttttttg tattatgtga ctaattagtt ggcatattgt taaaagtctc    3840
tcaaattagg ccagattcta aaacatgctg cagcaagagg accccgctct cttcaggaaa    3900
agtgttttca tttctcagga tgcttcttac ctgtcagagg aggtgacaag gcagtctctt    3960
gctctcttgg actcaccagg ctcctattga aggaaccacc cccattccta aatatgtgaa    4020
aagtcgccca aaatgcaacc ttgaaaggca ctactgactt tgttcttatt ggatactcct    4080
cttattattt ttccattaaa aataatagct ggctattata gaaaatttag accatacaga    4140
gatgtagaaa gaacataaat tgtccccatt accttaaggt aatcactgct aacaatttct    4200
ggatggtttt tcaagtctat ttttttttcta tgtatgtctc aattctcttt caaaatttta    4260
cagaatgtta tcatactaca tatatacttt ttatgtaagc tttttcactt agtattttat    4320
caaatatgtt tttattatat tcatagcctt cttaaacatt atatcaataa ttgcataata    4380
ggcaacctct agcgattacc ataattttgc tcattgaagg ctatctccag ttgatcattg    4440
ggatgagcat ctttgtgcat gaatcctatt gctgtatttg ggaaaatttt ccaaggttag    4500
attccaataa atatctcattt attattaaat attaaaatat ctatttatta ttaaaaccat    4560
ttataaggct ttttcataaa tgtatagcaa ataggaatta ttaacttgag cataagatat    4620
gagatacatg aacctgaact attaaaataa aatattatat ttaaccctta gtttaagaag    4680
aagtcaatat gcttatttaa atattatgga tggtgggcag atcacttgag gtcaggagtt    4740
cgagaccagc ctggccaaca tggcaaaacc acatctctac taaaaataaa aaaattagct    4800
gggtgtggtg gtgcactcct gtaatcccag ctactcagaa ggctgaggta caagaattgc    4860
tggaacctgg gaggcggagg ttgcagtgaa ccaagattgc accactgcac tccagccggg    4920
gtgacagagt gagactccga ctgaaaataa ataaataaat aaataaataa ataaataaat    4980
attatggatg gtgaagggaa tggtatagaa ttggagagat tatcttactg aacacctgta    5040
gtcccagctt tctctggaag tggtcgtatt tgagcaggat gtgcacaagg caattgaaat    5100
gcccataatt agtttctcag ctttgaatac actataaact cactggctga aggaggaaat    5160
tttagaagga agctactaaa agatctaatt tgaaaaacta caaaagcatt aactaaaaaa    5220
gtttattttc cttttgtctg ggcagtagtg aaaataacta ctcacaacat tcactatgtt    5280
tgcaaggaat taacacaaat aaaagatgcc ttttttactta aacaccaaga cagaaaactt    5340
gcccaatact gagaagcaac ttgcattaga gagggaactg ttaaatgttt tcaacccagt    5400
tcatctggtg gatgttttttg caggttactc tgagaatttt gcttatgaaa aatcattatt    5460
tttagtgtag ttcacaataa tgtattgaac atacttctaa tcaaaggtgc tatgtccttg    5520
tgtatggtac taaatgtgtc ctgtgtactt ttgcacaact gagaatcctg cagcttggtt    5580
taatgagtgt gttcatgaaa taaataatgg aggaattgtc a                         5621
```

<210> SEQ ID NO 2
<211> LENGTH: 1104
<212> TYPE: PRT
<213> ORGANISM: Homo sapiens

<400> SEQUENCE: 2

```
Met Ser Phe Arg Ala Ala Arg Leu Ser Met Arg Asn Arg Arg Asn Asp
1               5                   10                  15

Thr Leu Asp Ser Thr Arg Thr Leu Tyr Ser Ser Ala Ser Arg Ser Thr
                20                  25                  30

Asp Leu Ser Tyr Ser Glu Ser Asp Leu Val Asn Phe Ile Gln Ala Asn
            35                  40                  45
```

```
Phe Lys Lys Arg Glu Cys Val Phe Phe Thr Lys Asp Ser Lys Ala Thr
 50                  55                  60

Glu Asn Val Cys Lys Cys Gly Tyr Ala Gln Ser Gln His Met Glu Gly
 65                  70                  75                  80

Thr Gln Ile Asn Gln Ser Glu Lys Trp Asn Tyr Lys Lys His Thr Lys
                 85                  90                  95

Glu Phe Pro Thr Asp Ala Phe Gly Asp Ile Gln Phe Glu Thr Leu Gly
            100                 105                 110

Lys Lys Gly Lys Tyr Ile Arg Leu Ser Cys Asp Thr Asp Ala Glu Ile
        115                 120                 125

Leu Tyr Glu Leu Leu Thr Gln His Trp His Leu Lys Thr Pro Asn Leu
    130                 135                 140

Val Ile Ser Val Thr Gly Gly Ala Lys Asn Phe Ala Leu Lys Pro Arg
145                 150                 155                 160

Met Arg Lys Ile Phe Ser Arg Leu Ile Tyr Ile Ala Gln Ser Lys Gly
                165                 170                 175

Ala Trp Ile Leu Thr Gly Gly Thr His Tyr Gly Leu Met Lys Tyr Ile
            180                 185                 190

Gly Glu Val Val Arg Asp Asn Thr Ile Ser Arg Ser Glu Glu Asn
        195                 200                 205

Ile Val Ala Ile Gly Ile Ala Ala Trp Gly Met Val Ser Asn Arg Asp
210                 215                 220

Thr Leu Ile Arg Asn Cys Asp Ala Glu Gly Tyr Phe Leu Ala Gln Tyr
225                 230                 235                 240

Leu Met Asp Asp Phe Thr Arg Asp Pro Leu Tyr Ile Leu Asp Asn Asn
                245                 250                 255

His Thr His Leu Leu Val Asp Asn Gly Cys His Gly His Pro Thr
            260                 265                 270

Val Glu Ala Lys Leu Arg Asn Gln Leu Glu Lys Tyr Ile Ser Glu Arg
        275                 280                 285

Thr Ile Gln Asp Ser Asn Tyr Gly Gly Lys Ile Pro Ile Val Cys Phe
    290                 295                 300

Ala Gln Gly Gly Gly Lys Glu Thr Leu Lys Ala Ile Asn Thr Ser Ile
305                 310                 315                 320

Lys Asn Lys Ile Pro Cys Val Val Glu Gly Ser Gly Gln Ile Ala
                325                 330                 335

Asp Val Ile Ala Ser Leu Val Glu Val Glu Asp Ala Leu Thr Ser Ser
            340                 345                 350

Ala Val Lys Glu Lys Leu Val Arg Phe Leu Pro Arg Thr Val Ser Arg
        355                 360                 365

Leu Pro Glu Glu Thr Glu Ser Trp Ile Lys Trp Leu Lys Glu Ile
    370                 375                 380

Leu Glu Cys Ser His Leu Leu Thr Val Ile Lys Met Glu Glu Ala Gly
385                 390                 395                 400

Asp Glu Ile Val Ser Asn Ala Ile Ser Tyr Ala Leu Tyr Lys Ala Phe
                405                 410                 415

Ser Thr Ser Glu Gln Asp Lys Asp Asn Trp Asn Gly Gln Leu Lys Leu
            420                 425                 430

Leu Leu Glu Trp Asn Gln Leu Asp Leu Ala Asn Asp Glu Ile Phe Thr
        435                 440                 445

Asn Asp Arg Arg Trp Glu Ser Ala Asp Leu Gln Glu Val Met Phe Thr
    450                 455                 460

Ala Leu Ile Lys Asp Arg Pro Lys Phe Val Arg Leu Phe Leu Glu Asn
465                 470                 475                 480
```

```
Gly Leu Asn Leu Arg Lys Phe Leu Thr His Asp Val Leu Thr Glu Leu
                485                 490                 495

Phe Ser Asn His Phe Ser Thr Leu Val Tyr Arg Asn Leu Gln Ile Ala
            500                 505                 510

Lys Asn Ser Tyr Asn Asp Ala Leu Leu Thr Phe Val Trp Lys Leu Val
            515                 520                 525

Ala Asn Phe Arg Arg Gly Phe Arg Lys Glu Asp Arg Asn Gly Arg Asp
        530                 535                 540

Glu Met Asp Ile Glu Leu His Asp Val Ser Pro Ile Thr Arg His Pro
545                 550                 555                 560

Leu Gln Ala Leu Phe Ile Trp Ala Ile Leu Gln Asn Lys Lys Glu Leu
                565                 570                 575

Ser Lys Val Ile Trp Glu Gln Thr Arg Gly Cys Thr Leu Ala Ala Leu
            580                 585                 590

Gly Ala Ser Lys Leu Leu Lys Thr Leu Ala Lys Val Lys Asn Asp Ile
        595                 600                 605

Asn Ala Ala Gly Glu Ser Glu Glu Leu Ala Asn Glu Tyr Glu Thr Arg
    610                 615                 620

Ala Val Glu Leu Phe Thr Glu Cys Tyr Ser Ser Asp Glu Asp Leu Ala
625                 630                 635                 640

Glu Gln Leu Leu Val Tyr Ser Cys Glu Ala Trp Gly Gly Ser Asn Cys
                645                 650                 655

Leu Glu Leu Ala Val Glu Ala Thr Asp Gln His Phe Ile Ala Gln Pro
            660                 665                 670

Gly Val Gln Asn Phe Leu Ser Lys Gln Trp Tyr Gly Glu Ile Ser Arg
        675                 680                 685

Asp Thr Lys Asn Trp Lys Ile Ile Leu Cys Leu Phe Ile Ile Pro Leu
    690                 695                 700

Val Gly Cys Gly Phe Val Ser Phe Arg Lys Lys Pro Val Asp Lys His
705                 710                 715                 720

Lys Lys Leu Leu Trp Tyr Tyr Val Ala Phe Phe Thr Ser Pro Phe Val
                725                 730                 735

Val Phe Ser Trp Asn Val Val Phe Tyr Ile Ala Phe Leu Leu Leu Phe
            740                 745                 750

Ala Tyr Val Leu Leu Met Asp Phe His Ser Val Pro His Pro Pro Glu
        755                 760                 765

Leu Val Leu Tyr Ser Leu Val Phe Val Leu Phe Cys Asp Glu Val Arg
    770                 775                 780

Gln Trp Tyr Val Asn Gly Val Asn Tyr Phe Thr Asp Leu Trp Asn Val
785                 790                 795                 800

Met Asp Thr Leu Gly Leu Phe Tyr Phe Ile Ala Gly Ile Val Phe Arg
                805                 810                 815

Leu His Ser Ser Asn Lys Ser Ser Leu Tyr Ser Gly Arg Val Ile Phe
            820                 825                 830

Cys Leu Asp Tyr Ile Ile Phe Thr Leu Arg Leu Ile His Ile Phe Thr
        835                 840                 845

Val Ser Arg Asn Leu Gly Pro Lys Ile Ile Met Leu Gln Arg Met Leu
    850                 855                 860

Ile Asp Val Phe Phe Phe Leu Phe Leu Phe Ala Val Trp Met Val Ala
865                 870                 875                 880

Phe Gly Val Ala Arg Gln Gly Ile Leu Arg Gln Asn Glu Gln Arg Trp
                885                 890                 895

Arg Trp Ile Phe Arg Ser Val Ile Tyr Glu Pro Tyr Leu Ala Met Phe
```

|   |   |   | 900 |   |   |   | 905 |   |   |   | 910 |   |   |
|---|---|---|---|---|---|---|---|---|---|---|---|---|---|
| Gly | Gln | Val | Pro | Ser | Asp | Val | Asp | Gly | Thr | Thr | Tyr | Asp | Phe | Ala | His |
|   |   | 915 |   |   |   |   | 920 |   |   |   |   | 925 |   |   |   |
| Cys | Thr | Phe | Thr | Gly | Asn | Glu | Ser | Lys | Pro | Leu | Cys | Val | Glu | Leu | Asp |
|   |   | 930 |   |   |   |   | 935 |   |   |   |   | 940 |   |   |   |
| Glu | His | Asn | Leu | Pro | Arg | Phe | Pro | Glu | Trp | Ile | Thr | Ile | Pro | Leu | Val |
| 945 |   |   |   |   | 950 |   |   |   |   | 955 |   |   |   |   | 960 |
| Cys | Ile | Tyr | Met | Leu | Ser | Thr | Asn | Ile | Leu | Leu | Val | Asn | Leu | Leu | Val |
|   |   |   |   | 965 |   |   |   |   | 970 |   |   |   |   | 975 |   |
| Ala | Met | Phe | Gly | Tyr | Thr | Val | Gly | Thr | Val | Gln | Glu | Asn | Asn | Asp | Gln |
|   |   |   | 980 |   |   |   |   | 985 |   |   |   |   | 990 |   |   |
| Val | Trp | Lys | Phe | Gln | Arg | Tyr | Phe | Leu | Val | Gln | Glu | Tyr | Cys | Ser | Arg |
|   |   | 995 |   |   |   |   | 1000 |   |   |   |   | 1005 |   |   |   |
| Leu | Asn | Ile | Pro | Phe | Pro | Phe | Ile | Val | Phe | Ala | Tyr | Phe | Tyr | Met |
|   |   | 1010 |   |   |   |   | 1015 |   |   |   |   | 1020 |   |   |
| Val | Val | Lys | Lys | Cys | Phe | Lys | Cys | Cys | Cys | Lys | Glu | Lys | Asn | Met |
|   |   | 1025 |   |   |   |   | 1030 |   |   |   |   | 1035 |   |   |
| Glu | Ser | Ser | Val | Cys | Cys | Phe | Lys | Asn | Glu | Asp | Asn | Glu | Thr | Leu |
|   |   | 1040 |   |   |   |   | 1045 |   |   |   |   | 1050 |   |   |
| Ala | Trp | Glu | Gly | Val | Met | Lys | Glu | Asn | Tyr | Leu | Val | Lys | Ile | Asn |
|   |   | 1055 |   |   |   |   | 1060 |   |   |   |   | 1065 |   |   |
| Thr | Lys | Ala | Asn | Asp | Thr | Ser | Glu | Glu | Met | Arg | His | Arg | Phe | Arg |
|   |   | 1070 |   |   |   |   | 1075 |   |   |   |   | 1080 |   |   |
| Gln | Leu | Asp | Thr | Lys | Leu | Asn | Asp | Leu | Lys | Gly | Leu | Leu | Lys | Glu |
|   |   | 1085 |   |   |   |   | 1090 |   |   |   |   | 1095 |   |   |
| Ile | Ala | Asn | Lys | Ile | Lys |
|   |   | 1100 |   |   |   |